(12) United States Patent
Landry

(10) Patent No.: US 7,156,110 B2
(45) Date of Patent: Jan. 2, 2007

(54) DENTAL FLOSS DISPENSING AND TENSIONING DEVICE

(76) Inventor: David H. Landry, 1445 Semlin Drive, Vancouver, British Columbia (CA) V5L 4K4

( * ) Notice: Subject to any disclaimer, the term of this patent is extended or adjusted under 35 U.S.C. 154(b) by 273 days.

(21) Appl. No.: 10/890,163

(22) Filed: Jul. 14, 2004

(65) Prior Publication Data

US 2006/0011211 A1 Jan. 19, 2006

(51) Int. Cl.
*A61C 15/04* (2006.01)
(52) U.S. Cl. .................................................. 132/325
(58) Field of Classification Search ................ 132/324, 132/325, 326, 327
See application file for complete search history.

(56) References Cited

U.S. PATENT DOCUMENTS

| 861,254 | A | | 7/1907 | Braime |
|---|---|---|---|---|
| 3,734,107 | A | * | 5/1973 | Thierman .................... 132/325 |
| 5,038,806 | A | | 8/1991 | Ewald |
| 5,060,681 | A | * | 10/1991 | Westbrook et al. ......... 132/325 |
| 5,678,578 | A | * | 10/1997 | Kossak et al. .............. 132/322 |
| 5,816,271 | A | * | 10/1998 | Urso ........................... 132/322 |
| 5,819,769 | A | | 10/1998 | Gutierrez |
| 5,823,207 | A | | 10/1998 | Bushman |
| 6,161,556 | A | | 12/2000 | Gutierrez |
| 6,874,509 | B1 | * | 4/2005 | Bergman .................... 132/325 |
| 2002/0078974 | A1 | * | 6/2002 | Kossak et al. .............. 132/325 |

OTHER PUBLICATIONS

Printout of FLOSSBRITE website dated Mar. 21, 2004.

* cited by examiner

*Primary Examiner*—Todd E. Manahan
(74) *Attorney, Agent, or Firm*—Oyen Wiggs Green & Mutala LLP

(57) ABSTRACT

A hand-held dental floss holder, dispenser, floss tensioning, and floss advancing device. The device is configured with one end being a handle and the other being a pair of tips across which dental floss is spanned for presenting to inter-dental spaces. An internal supply of dental floss is housed inside the handle. The floss passes from the supply, moves around floss guides, wraps one or more times around a free spooling clutch spool, exits the body of the device through an opening and is directed to and across the tips of the device and is guided back to a collection spool rotationally connected to a manually-activated one way thumbwheel. In a first position, the gearing of a gear assembly and an internal clutch spool assembly causes the floss to tension when the thumbwheel is turned. In a second position, the disengagement of gearing allows the clutch spool to spool freely, allowing fresh floss to be substituted for used floss, when the thumbwheel is turned.

5 Claims, 11 Drawing Sheets

DENTAL FLOSS DISPENSING AND TENSIONING DEVICE

TECHNICAL FIELD

The present invention relates to devices for easing the chore of flossing with dental floss, and more particularly relates to hand-held devices which dispense and tension fresh dental floss for use by a user, and which concurrently spool used dental floss.

BACKGROUND

Daily flossing is an integral part of a complete oral hygiene program. Brushing one's teeth without flossing leaves a large portion of the tooth surfaces uncleaned. Flossing helps to remove harmful plaque and bacteria from between teeth, where a toothbrush can't reach. It is well known that plaque build-up can lead to gum disease, chronic bad breath, tooth loss and other ailments. Even with these risks, most adults do not floss on a regular basis.

This is largely because traditional flossing methods are awkward, difficult and painful to many people, causing them to skip the important step of flossing. Apart from mere laziness, there are other reasons people don't floss. These include spatial interference (when one's hands are too large to properly manipulate floss within one's mouth, or when an adult, for example, is attempting to floss a child's teeth), loss of circulation (floss wrapped tightly around a fingertip cuts off circulation to the tip of the finger, a painful and unpleasant situation), disability (arthritis or any other disability affecting manual dexterity can limit or prevent the proper manipulation of floss), and the general unhygienic nature of the process (hands are in contact with used floss, and must be placed repeatedly deep within the mouth). Flossing is also simply generally inconvenient, requiring concentration, the use of two hands at all times, and time to prepare a new section of floss for each tooth.

To ease the inconvenience of flossing, a large variety of flossing devices have been suggested, among them those disclosed in the following U.S. Pat. Nos. 3,734,107, 5,038,806, 5,819,769 5,823,207, 6,161,556, and also in U.S. patent application No. US2002/0170570.

All of these prior art dental floss systems have disadvantages that keep them from being commonly used. Some are very complicated in structure and expensive to produce. Some do not permit the easy substitution of new floss for used floss. Some require two hands to operate. There remains, accordingly, a need for a relatively simple dental floss dispensing device that is easily operated with one hand.

SUMMARY OF INVENTION

The present invention is a dental floss dispensing device which has a thumbwheel for operation by a single thumb or finger, to allow a user to dispense floss, hold, advance and properly tension it, and to collect used floss.

The device, in a preferred embodiment, is hand-held and has a handle portion having a semi-hollow interior. Attached to or formed at one end of the handle portion is a flossing portion bearing a pair of arms for supporting between them a length of dental floss for insertion by a user between a pair of teeth.

Within the interior of the handle portion are contained, at least partially, two geared assemblies, a "gear assembly" and a "clutch spool assembly". The gear assembly is fixed within notches formed in the handle portion, and has an axle supported by the handle portion. The axle bears a thumbwheel for turning the axle, a used-floss collection spool, and an axle gear, with at least the axle gear being contained within the interior of the handle portion. The clutch spool assembly is completely supported and contained within the interior of the handle portion, and comprises a clutch spool having a clutch gear attached to one side thereof.

When a length of floss is threaded in the device from a spool of floss contained within the interior of the handle portion to and around the clutch spool, and then from the clutch spool out of the body of the device to a tip of one of the arms (the first arm), then from the first arm to the second arm, and then from the second arm to the used-floss collection spool, the gear assembly is manipulable by manipulating the thumbwheel into a first position wherein the axle gear of the gear assembly is engaged with the clutch gear of the clutch spool assembly, thereby tensioning the floss between the arms of the flossing portion by causing the collection spool and the clutch spool to turn in opposite directions when the thumbwheel is turned in a first direction. The thumbwheel may be prevented from being turned in the other direction by a pawl acting on ridges or grooves formed on the circumference or face or side of the thumbwheel.

So, while the thumbwheel is in a position wherein the axle gear and clutch gear are engaged, floss becomes tensioned and cannot move through the device. However, the gear assembly may also be manipulated by manipulating the thumbwheel into a second position wherein the axle gear is disengaged with the clutch gear of the clutch spool assembly. This allows the clutch gear to spool freely in the same direction as the collection spool, allowing at least a portion of the length of floss to be taken up onto the collection spool, and a fresh portion of floss to be advanced onto and suspended between the arms of the device.

In the preferred embodiment, the gear assembly is normally urged into the first, engaged position by springs applying force to the axle.

Used floss is taken up on an externally mounted collection spool. For sanitary and hygienic purposes used floss can be easily removed after each use. A cutter is included for this purpose. The collection wheel and all surfaces that make contact with the used floss are fully accessible for easy cleaning and disinfecting. No contact of the floss by the user's hands is required other than to cut and dispose of the used floss after flossing. The device is disposable or may be reused.

BRIEF DESCRIPTION OF DRAWINGS

It will be appreciated that the particularized description of the invention described briefly above and which follows hereafter is rendered by reference to certain specific embodiments of the invention which are illustrated in the appended drawings. The drawings depict only one typical embodiment of the invention and are not therefore to be considered to be limiting of the scope of the invention.

Accordingly, in the accompanying drawings which illustrate a specific embodiment of the invention, but which should not be construed as restricting the spirit or scope of the invention in any way.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
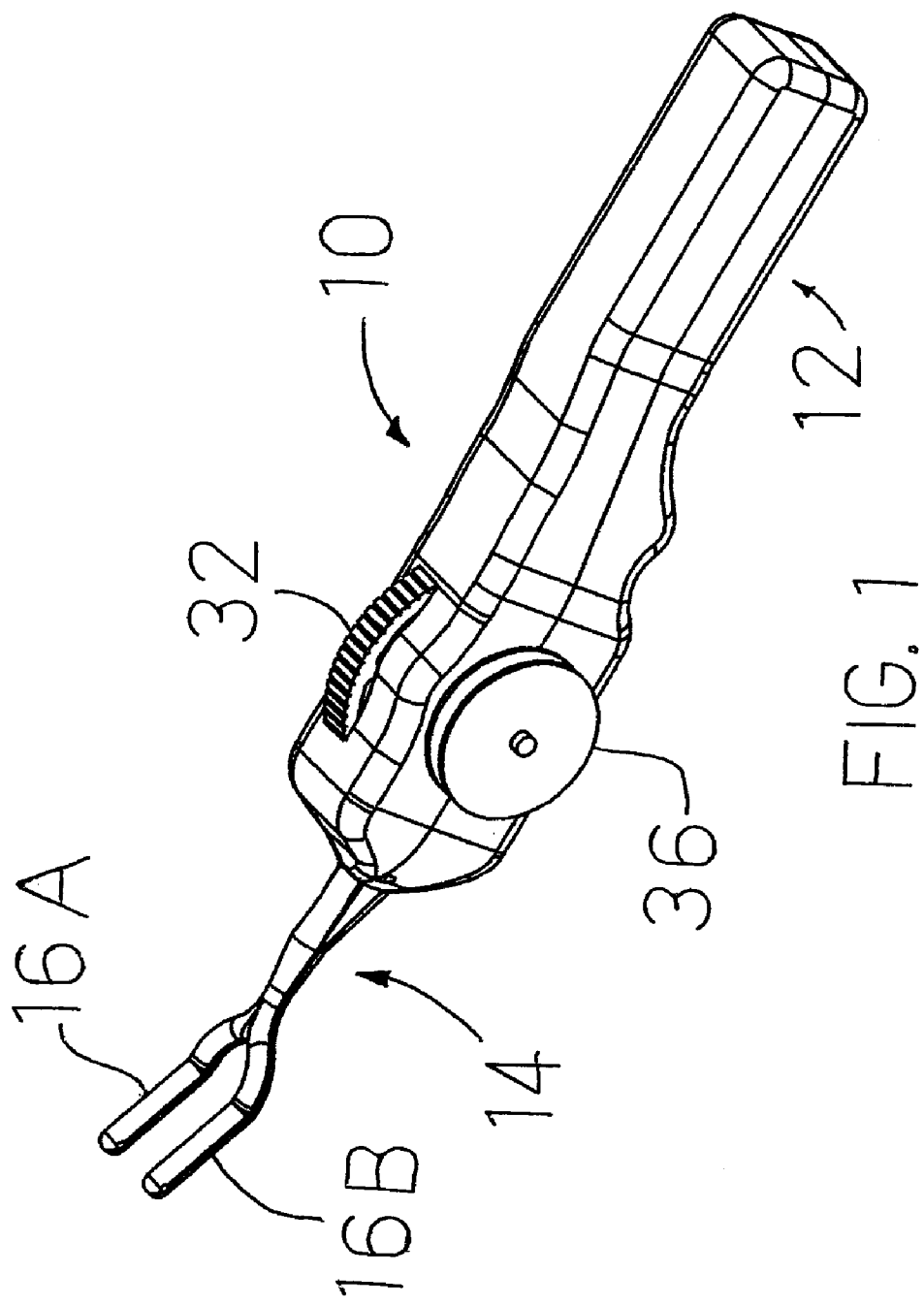
FIG. 1 is a top perspective view of a flossing device made in accordance with one embodiment of the present invention.

Referring first to FIG. 1, the present invention provides a device which dispenses, holds, tensions, collects and cuts dental floss for use by a user. The flossing device, referred to generally herein by reference numeral "10" has, generally, a handle portion 12 for allowing a user to hold and manipulate the device, and a flossing portion 14 for insertion into the mouth of a user to floss between the user's teeth. The handle portion 12 may be of any suitable size or shape which allows the device to contain a spool of floss and the gear assembly and clutch spool assembly of the invention as described below.

As shown in FIG. 1, in a preferred embodiment of the invention the flossing portion 14 of device 10 ends in a pair of arms, first arm 16A and second arm 16B. Arms 16A, 16B are intended to support a usable length of dental floss between them, as described further below.

Figure 2:
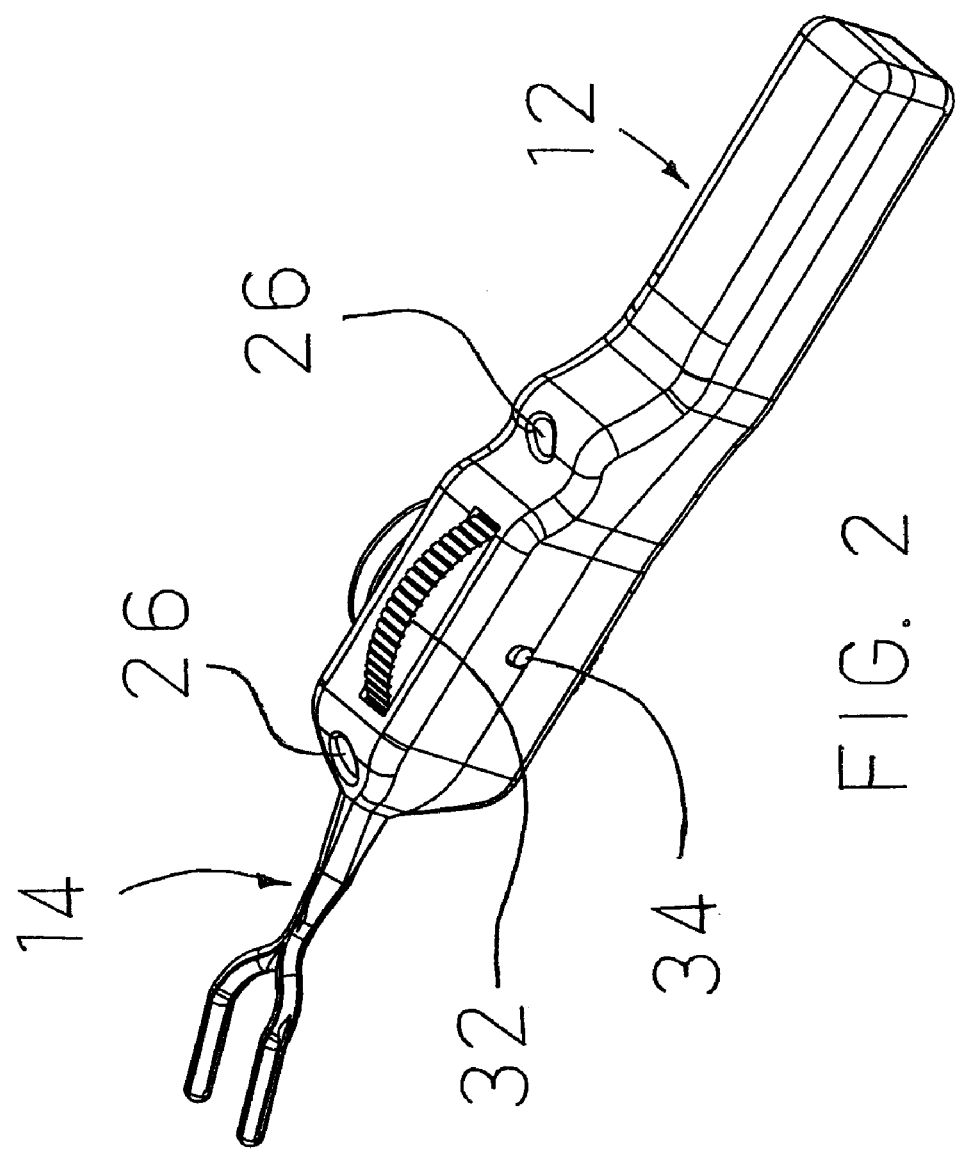
FIG. 2 is bottom perspective view of the flossing device shown in FIG. 1.

FIG. 2 shows the underside of device 10. It will be appreciated that it may be convenient for device 10 to be able to be opened by a user to replace an empty spool of floss within the device 10. To this end, it is proposed in the illustrated embodiment of the invention that the handle portion 12 of device 10 be constructed of a bottom portion 70 and a top portion 80, as shown more clearly respectively in FIGS. 3 and 4. The top and bottom portions 80, 70 of handle portion 12 may be attached to one another with screws 26 (FIG. 2) which pass through screw bosses 25 (FIGS. 3 and 4) on the inside of one or both of the top or bottom portions 80, 70 of handle portion 12. Of course, it is not necessary to the invention that the device 10 be openable, as it is foreseen that disposable versions of the device could be manufactured.

Figure 4:
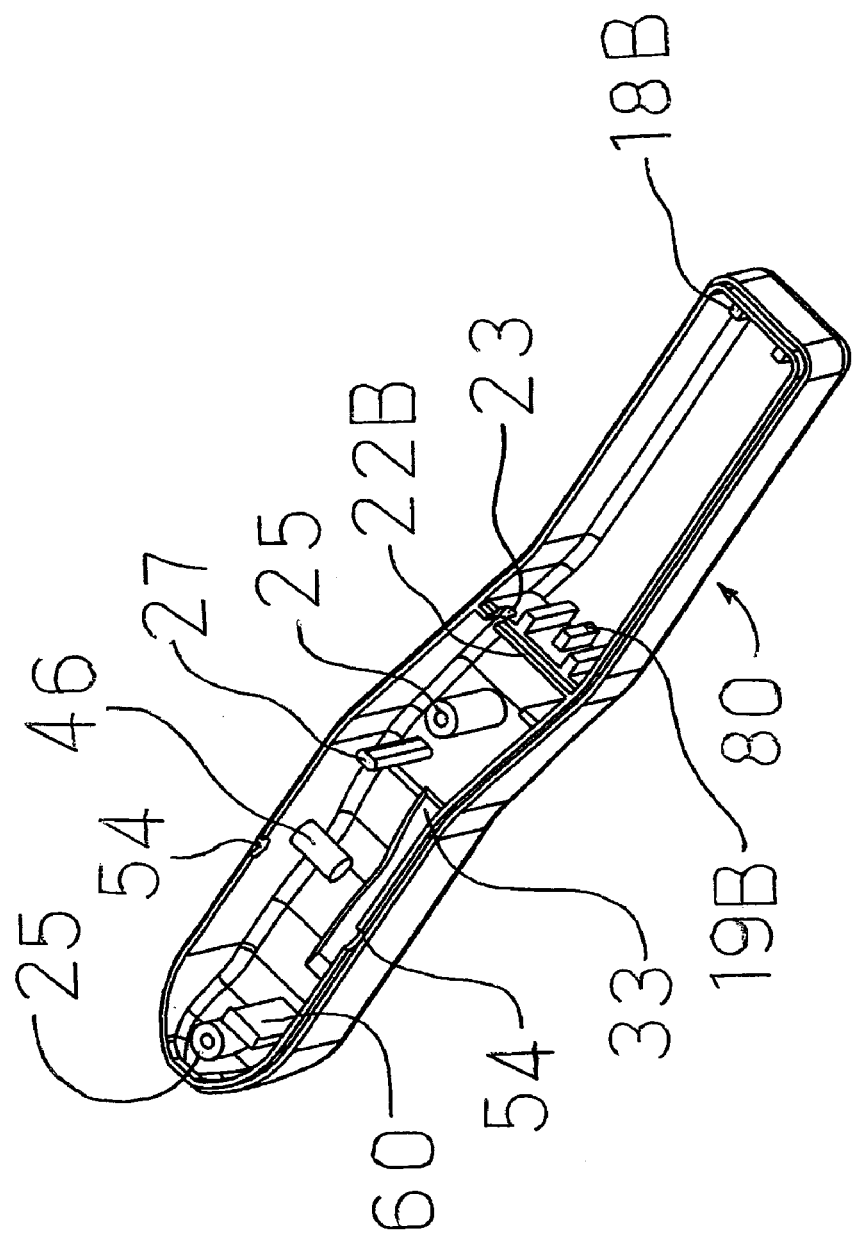
FIG. 4 is a perspective view of the top portion of the flossing device shown in FIG. 1, showing the interior of the top portion of the device.
Figure 5:
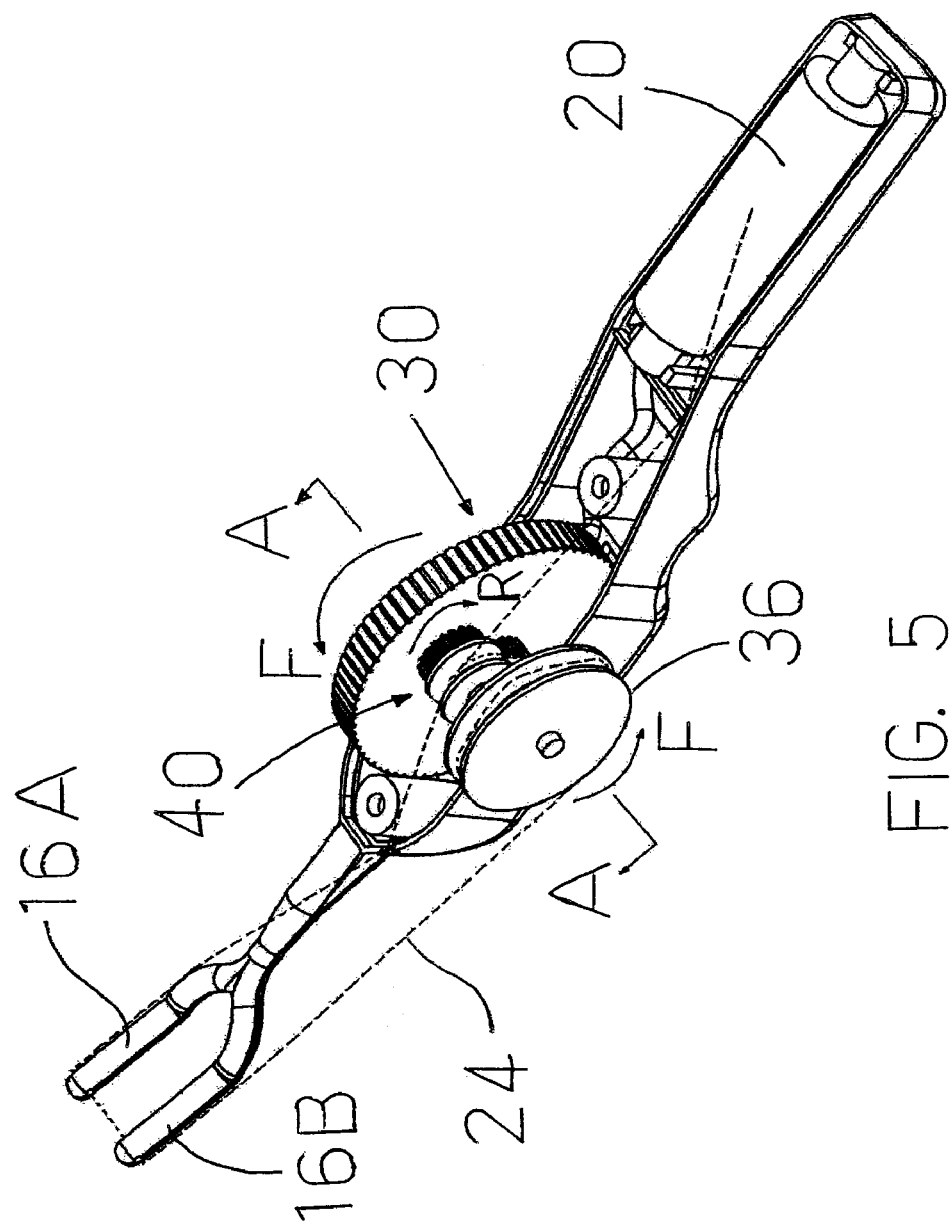
FIG. 5 is a perspective view of the bottom portion of the flossing device as shown in FIG. 3, showing a spool of floss, the gear assembly and the clutch spool assembly of the device in place, and showing floss extending from the floss spool to the floss collection spool.

As shown in FIG. 5, the device 10 is configured to house a spool of floss 20. Of course, it is not necessary for the floss to be supplied on a spool, but this preferred arrangement is shown in the drawings. In the preferred embodiment, spool 20 is supported by front and rear spool supports 18A, 18B, 19A and 19B (seen in FIGS. 3 and 4). A wall 22A, 22B may be provided within the device 10 to totally enclose spool 20. If this wall is provided, then a slot 23 must also be provided to allow a strand of floss to pass through the wall from the spool 20. As is typical with other hand-held flossing devices, a strand of floss 24 may be directed from the spool 20 to first arm 16A, then across to second arm 16B and then to a collection spool 36. The usable portion of floss 24 is the portion supported between arms 16A and 16B. "Fresh" floss is therefore dispensed from spool 20, and "used" floss collected on collection spool 36.

As will be appreciated, however, if the strand of floss 24 is not tensioned between arms 16A and 16B, it will be too limp to be usable by a user. So, it is an object of the invention to provide means for tensioning the floss 24 for a period of time for use by a user by not allowing fresh floss to spool "forward" from spool 20, and concurrently by not allowing used floss which has already been spooled onto collection spool 36 to return "backwards" towards arms 16A, 16B.

Figure 7:
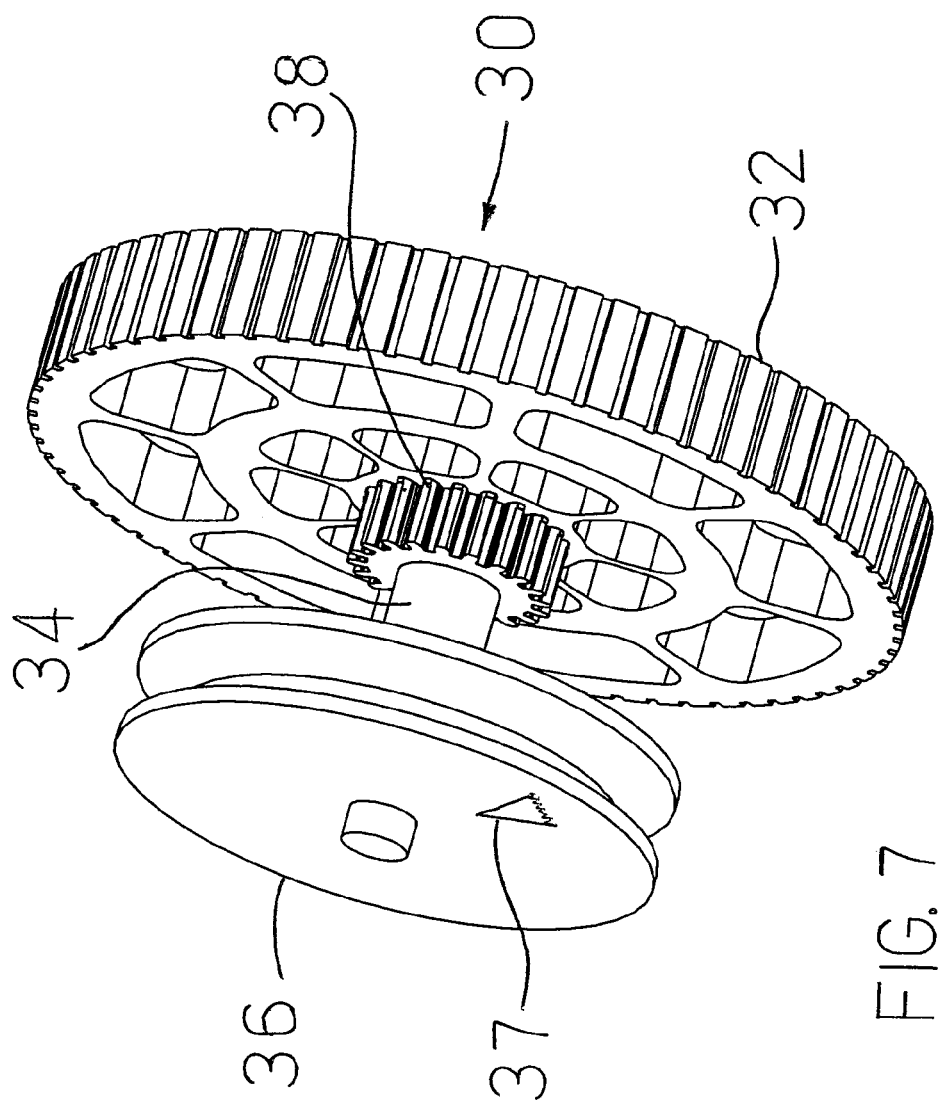
FIG. 7 is a perspective view of the gear assembly of the present device shown in FIG. 1.
Figure 11:
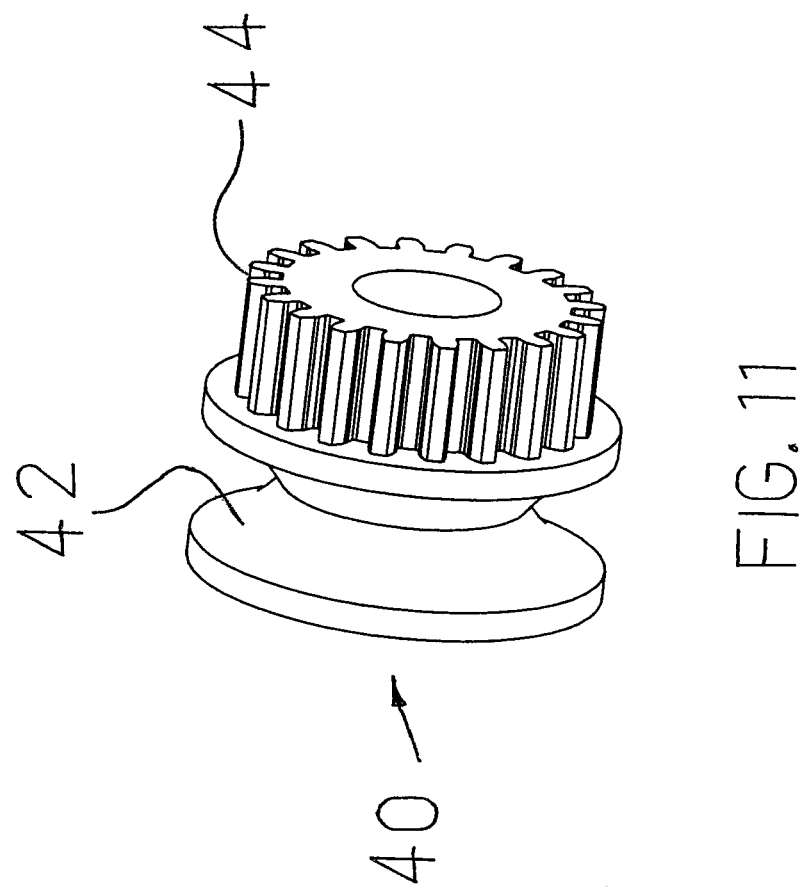
FIG. 11 is a perspective view of the clutch spool assembly shown in FIG. 10.

This is accomplished in the present invention by an ingenious combination of two geared assemblies contained at least partially within the device 10. FIGS. 7 and 11 provide perspective views of the two geared assemblies of the invention.

As shown in detail in FIG. 7, the device 10 has a gear assembly 30 which has an axle 34. Axle 34 bears upon it a thumbwheel 32 for allowing a user to turn the assembly 30 when it is contained in place within device 10. Axle 34 also bears upon it the collection spool 36 previously described. Also borne on axle 34 is what is hereafter termed an "axle gear" 38, which in a preferred embodiment is located at or near thumbwheel 32.

Figure 10:
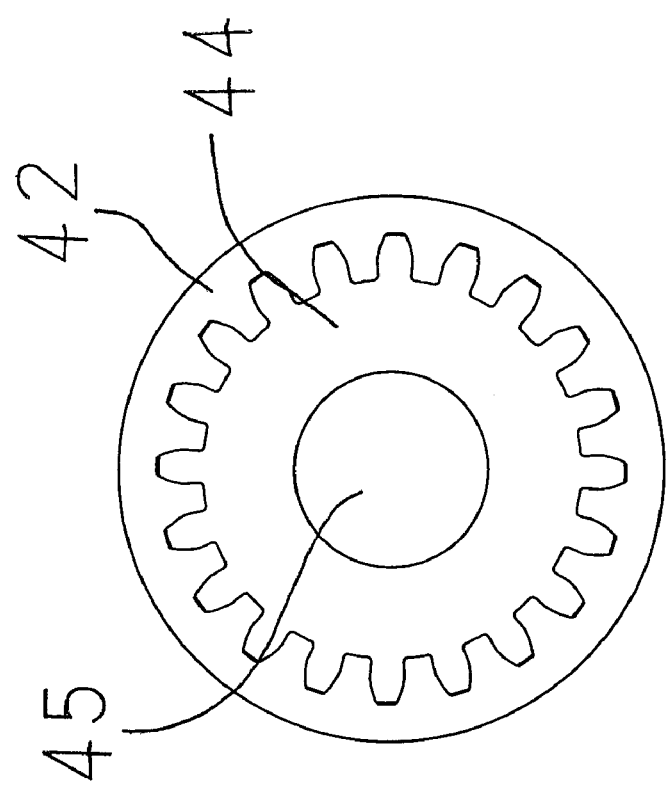
FIG. 10 is a side view of the clutch spool assembly of the device shown in the Figures.

As shown in FIG. 11, the device also has what is termed herein a "clutch spool assembly" 40. Clutch spool assembly 40 has a clutch spool 42 having attached to one side thereof a clutch gear 44. Clutch spool assembly 40 is also shown in side view in FIG. 10. Clutch gear 44 has gear teeth which are sized and configured to mate with the gear teeth of axle gear 38 of gear assembly 30. Clutch spool assembly 40 may have a bore 45 formed therethrough to allow assembly 40 to be held in place within device 10.

Figure 3:
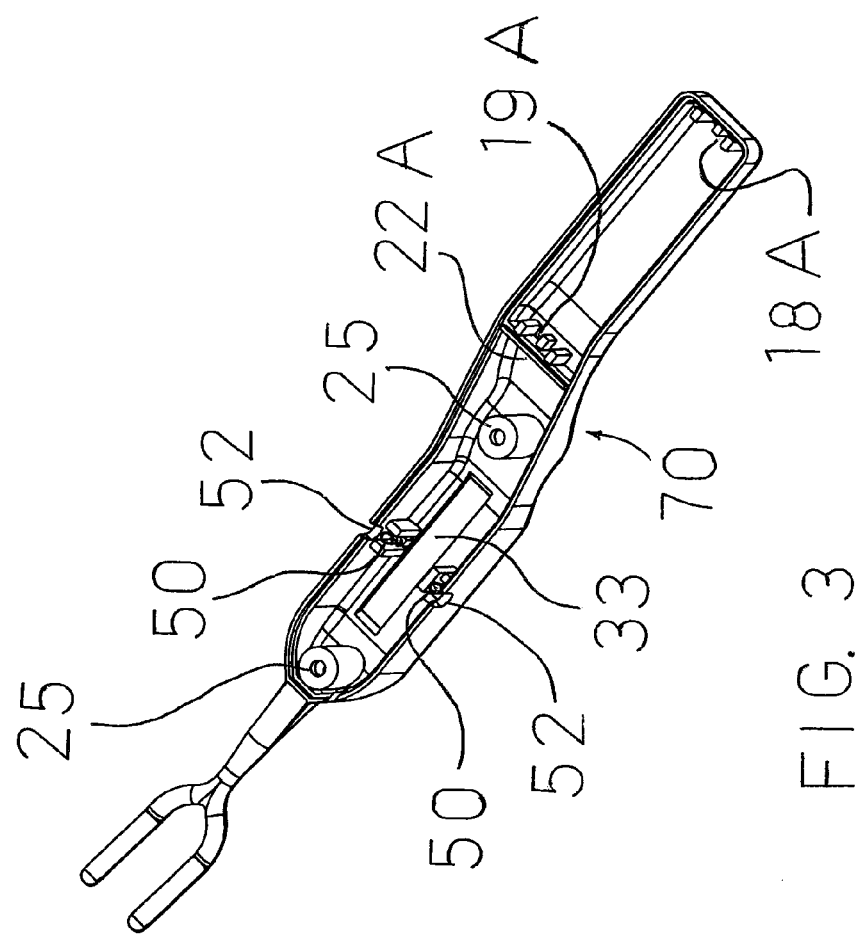
FIG. 3 is a perspective view of the bottom portion of the flossing device shown in FIG. 1, showing the interior of the bottom portion.

The top and bottom portions 80, 70 of device 10 are configured to accept and hold in place gear assembly 30 and clutch spool assembly 40. For example, as shown in FIGS. 3 and 4, each one of the bottom and top portions 70, 80 of device 10 has a rectangular opening formed therethrough, for allowing thumbwheel 32 of gear assembly to protrude therethrough when gear assembly is in place within the device. FIG. 1 illustrates how thumbwheel 32 protrudes through the top portion 80 of device 10, and FIG. 2 shows thumbwheel 32 protruding through the bottom portion 70 of device 10.

It will be appreciated from the figures that axle 34 of gear assembly 30 is held in place and supported at least partially by the side walls of the top and bottom portions 80, 70 of handle 12 of device 10. As shown in FIG. 3, the bottom portion 70 of handle 12 has oblong notches 52 formed in the sides thereof. Similarly, the top portion 80 of handle 12 has semicircular notches 54 formed in the sides thereof (FIG. 4). Notches 52 and 54 face one another when the top and bottom portions 80, 70 are connected by screws 26.

As shown in FIG. 5, gear assembly 30 is contained within device 10 by fitting axle 34 within notches 52 and 54, with the notches 52, 54 able to act as bearings for axle 34. Thumbwheel 32 is contained within device 10 (but for the portions which protrude from the top and bottom portions of handle 12), as is axle gear 38. Collection spool 36 is preferably outside of the device, but may be alternatively enclosed within the device. Axle 34 can also be seen to be supported by the walls of the handle 12 in FIG. 2.

Figure 6:
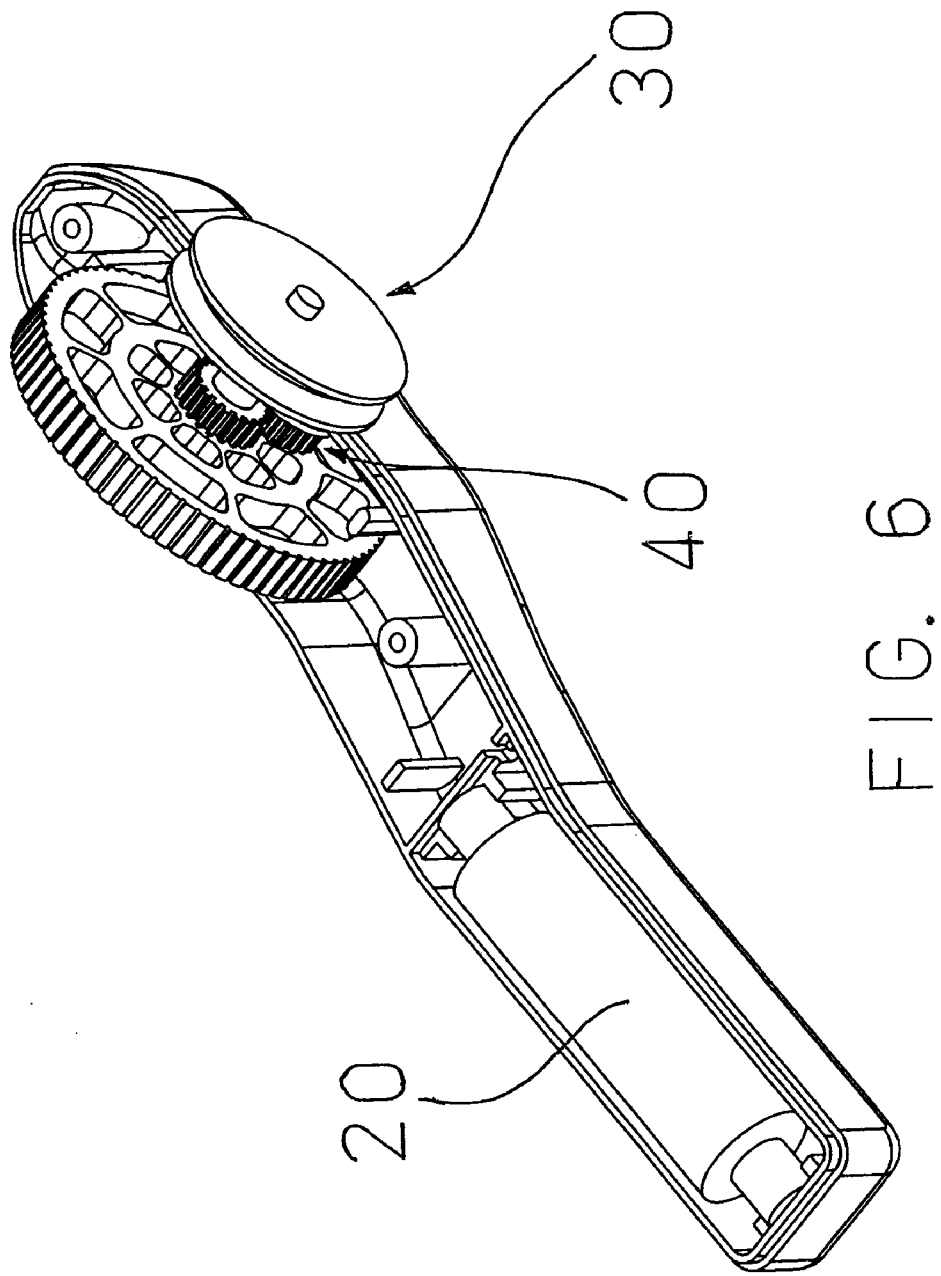
FIG. 6 is a perspective view of the top portion of the flossing device as shown in FIG. 4, showing the gear assembly of the device as it would occupy space in the top portion when in place.

In the preferred embodiment shown in the figures, the clutch spool assembly 40 is also fitted within the handle 12 of the device 10 so that clutch gear 44 is capable of mating with axle gear 38, as shown in FIGS. 5 and 6. This is conveniently accomplished by providing a shaft 46 (FIG. 4) on the side wall of the top portion 80 of handle 12. The bore 45 of clutch spool assembly 40 is suitably sized to allow clutch spool assembly 40 to fit onto shaft 46 and to rotate freely thereon.

As shown in FIG. 5, in operation a strand of floss is taken from spool 20, and wound once or more times around clutch spool 42. From clutch spool 42, the strand of floss extends forwardly and exits handle 12 to the flossing potion 14 of device 10. Floss 24 is then passed to the tip or near to the tip of first arm 16A, across to the tip of arm 16B, and from arm 16B to collection spool 36. Collection spool 36 may have a cutting device 37 (FIG. 7) mounted or formed thereon for cutting floss 24. Cutting device 37 may also be mounted upon handle portion 12 or flossing portion 14. One or more guides 27 may assist in directing the path of the floss.

Figure 8:
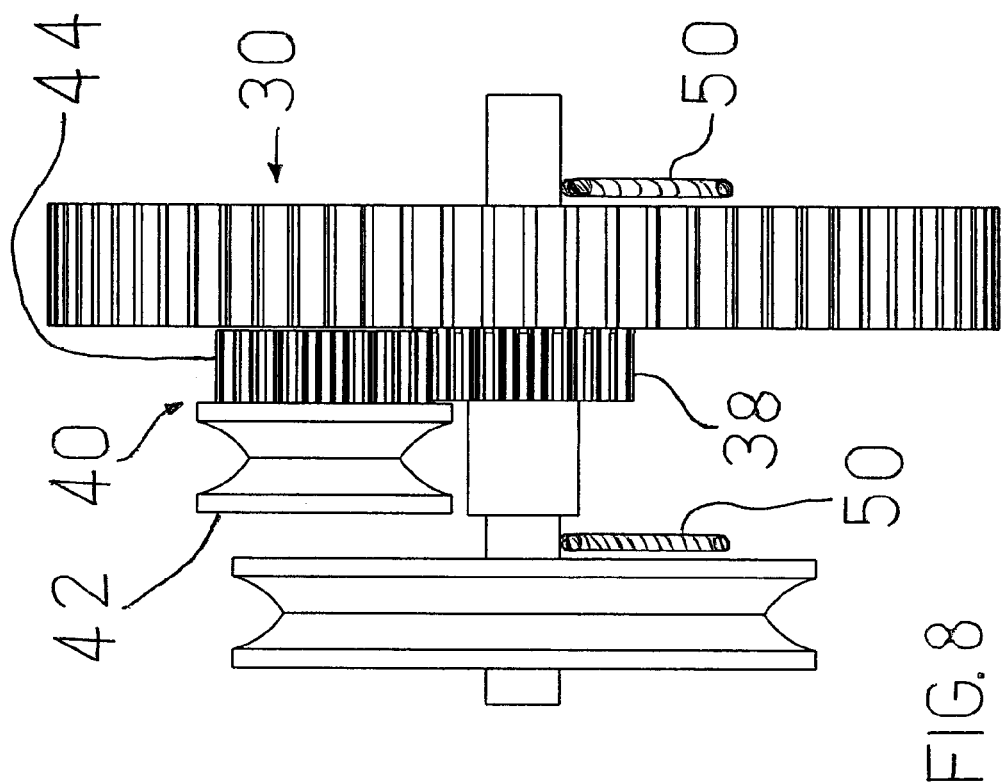
FIG. 8 is a partially schematic cross-sectional view of the gear assembly and clutch spool assembly of the device shown in FIG. 1, taken in cross section along line A—A shown in FIG. 5, with the gear assembly urged into an engaged position wherein it is in geared engagement with the clutch spool assembly.
Figure 9:
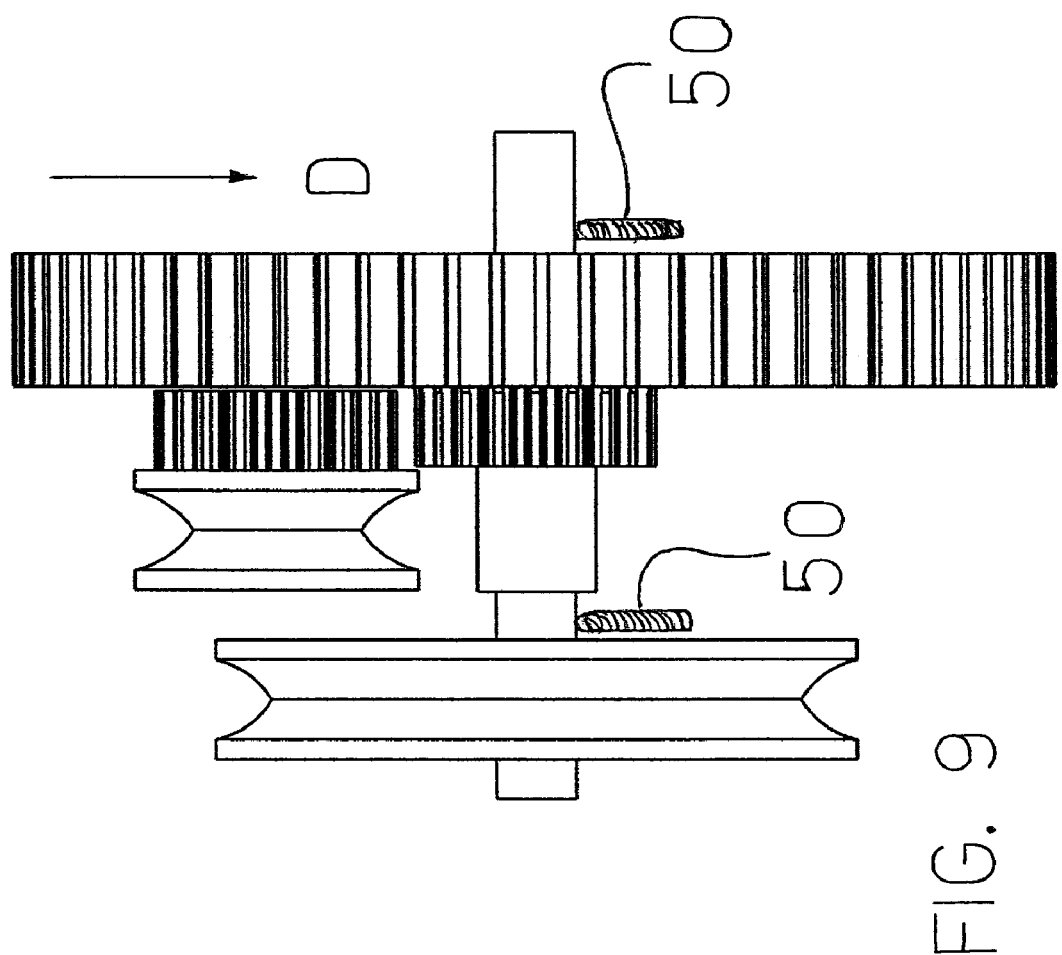
FIG. 9 is a partially schematic cross-sectional view of the gear assembly and clutch spool assembly of the device shown in FIG. 1, looked at end-on, generally along line A—A shown in FIG. 5, similar to the view shown in FIG. 8, but with the gear assembly forced downwardly so that it in an unengaged position.

The engagement relationship between gear assembly 40 and clutch spool assembly 40 is illustrated in FIGS. 8 and 9.

In a first position, shown in FIG. 8, the axle gear 38 of gear assembly 30 and the clutch gear 44 of clutch spool assembly 40 engage one another, so that when one of gear assembly 30 and clutch spool assembly 40 is turned, the other assembly turns also, but in the opposite direction. In the preferred embodiment of the invention, springs 50 (FIG. 3) normally urge gear assembly 30 into this engaged position with clutch spool assembly 40. As shown in FIG. 5, when in this engaged position, if thumbwheel 32 is turned forwardly by a user in a direction "F", this causes collection spool 36 and axle gear 38 to turn in the same direction "F". However, the turning of axle gear in direction "F" causes the clutch gear 44 to turn in the opposite direction, "R". It will thus be appreciated that if there is enough frictional force between the floss 24 and the surface of clutch spool 42, and also between the floss 24 and the surface of collection spool 36, the turning of the thumbwheel 32 will tend to cause floss 24 to be pulled forwardly onto collection spool 36 and also backwardly onto clutch spool 42, thereby tensioning floss 24. The frictional force exerted by the floss can be increased by constructing the outer surface of the clutch spool of a material with sufficient surface frictional coefficient to prevent floss from slipping under tension when wrapped once around said clutch spool. Or, the floss can be wrapped two or three times around the spool to ensure enough friction.

So, a length of floss having the foregoing discussed arrangement within device 10 can be tensioned by turning the thumbwheel of the device forwardly. However, it is also necessary to supply a new supply of floss between the arms 16A and 16B from time to time, and to collect used floss onto collection spool 36. This is accomplished by disengaging gear assembly 30 from clutch spool assembly 40.

As shown in FIG. 9, this is accomplished in the device 10 by pushing gear assembly 30 downwardly in the direction "D" against the force exerted by springs 50 and then turning thumbwheel 32. It will be appreciated that the oblong nature of notches 52 allows for axle 34 of gear assembly 30 to move downwardly into notches 52. Again considering FIG. 5, when in this disengaged position, the turning of gear assembly 30 in the direction "F" causes collection spool 36 and axle gear 38 to turn in the same direction "F". However, in this position, axle gear 38 is not engaged with clutch gear 44 and accordingly does not force clutch gear 44 to turn in the opposite direction, "R". Rather, clutch assembly 40 spools freely in direction F, and fresh floss 24 is passed from spool 20, around clutch spool 42, and to arms 16A, 16B. Once fresh floss passes to between arms 16A and 16B, the user releases pressure on thumbwheel 32, allowing the engagement of gears 38 and 44, thereby permitting the tensioning of floss by turning thumbwheel 32, as previously discussed.

It will be recognized that to maintain the floss in a tensioned state it is necessary not to allow thumbwheel 32 to turn "backwards" in the direction "R". While the user could accomplish this by maintaining "forward" pressure on thumbwheel 32, it is convenient to provide a pawl 60 (FIG. 4) to act on teeth or ridges 62 formed on thumbwheel 32. Conveniently, ridges 62 on thumbwheel 32 also serve to provide a user with a better grip on thumbwheel 32.

It will be appreciated that what is important to the invention is the interaction between gear assembly 30 and clutch assembly 40. The particular path taken by floss 24 is not vital to the invention. Accordingly, it is recognized that floss 24 could pass entirely through the device 10 to the tip of arm 16A. Similarly, although the Figures show floss 24 being threaded through holes formed in the tips of arms 16A, 16B, the floss could simply be held on arms 16A 16B in grooves formed at the tips of the arms.

As will be apparent to those skilled in the art in the light of the foregoing disclosure, many alterations and modifications are possible in the practice of this invention without departing from the spirit or scope thereof. For example, although the embodiment of the invention shown in the drawings has screws 26 attaching top and bottom portions 80, 70 to one another, snapping tabs could be used in their place.

Accordingly, the scope of the invention is to be construed in accordance with the substance defined by the following claims.

What is claimed is:

1. A device for dispensing and tensioning dental floss, the device comprising:
   a) a handle portion having an interior and an exterior;
   b) a flossing portion attached to the handle portion, the flossing portion bearing first and second arms for supporting a length of dental floss between them;
   c) a gear assembly supported by and partially contained within the interior of the handle portion, the gear assembly comprising an axle supported by the handle portion, the axle bearing a thumbwheel for turning the axle, a used-floss collection spool, and an axle gear, at least the axle gear being contained within the interior of the handle portion; and
   d) a clutch spool assembly supported and contained within the interior of the handle portion, the clutch spool assembly comprising a clutch spool having a clutch gear attached to one side thereof;

wherein when a length of floss is threaded from a spool of floss contained within the interior of the handle portion to the clutch spool, then from the clutch spool out of the device to the tip of the first arm, then from the first arm to the second arm, and then from the second arm to the used-floss collection spool, the gear assembly is manipulable by manipulating said thumbwheel into a first position wherein the axle gear of the gear assembly is engaged with the clutch gear of the clutch spool assembly, thereby tensioning the floss between the arms of the flossing portion by causing the collection spool and the clutch spool to turn in opposite directions when the thumbwheel is turned in a first direction.

2. The device as claimed in claim 1, wherein the gear assembly is manipulable by manipulating said thumbwheel into a second position wherein the axle gear is disengaged with the clutch gear of the clutch spool assembly, thereby allowing the clutch gear to spool freely in the same direction as the collection spool, allowing at least a portion of the length of floss to be taken up onto the collection spool.

3. The device of claim 2 wherein the gear assembly is normally urged into the first, engaged position by springs applying force to the axle.

4. The device of claim 3 wherein the thumbwheel has ridges on its circumference and wherein the thumbwheel is prevented from turning in a second direction by a pawl contained within the handle portion acting on the ridges.

5. The device of claim 3 wherein the thumbwheel has ridges on its face and wherein the thumbwheel is prevented from turning in a second direction by a pawl contained within the handle portion acting on the ridges.

* * * * *